United States Patent
Tian et al.

(10) Patent No.: US 12,136,146 B1
(45) Date of Patent: Nov. 5, 2024

(54) SYSTEM FOR RECONSTRUCTING MAGNETIC PARTICLE IMAGE BASED ON PRE-TRAINED MODEL

(71) Applicant: INSTITUTE OF AUTOMATION, CHINESE ACADEMY OF SCIENCES, Beijing (CN)

(72) Inventors: Jie Tian, Beijing (CN); Zechen Wei, Beijing (CN); Hui Hui, Beijing (CN); Xin Yang, Beijing (CN)

(73) Assignee: INSTITUTE OF AUTOMATION, CHINESE ACADEMY OF SCIENCES, Beijing (CN)

( * ) Notice: Subject to any disclaimer, the term of this patent is extended or adjusted under 35 U.S.C. 154(b) by 0 days.

(21) Appl. No.: 18/752,758

(22) Filed: Jun. 24, 2024

(30) Foreign Application Priority Data

Jun. 26, 2023 (CN) .......................... 202310753529.X

(51) Int. Cl.
  *G06T 11/00* (2006.01)
  *A61B 5/0515* (2021.01)
  *G06T 3/4046* (2024.01)

(52) U.S. Cl.
  CPC .......... *G06T 11/006* (2013.01); *A61B 5/0515* (2013.01); *G06T 3/4046* (2013.01); *G06T 2210/41* (2013.01); *G06T 2211/441* (2023.08)

(58) Field of Classification Search
  None
  See application file for complete search history.

(56) References Cited

U.S. PATENT DOCUMENTS

2020/0066006 A1* 2/2020 Dwivedi ................ G16H 30/40
2023/0021926 A1* 1/2023 Zhao .................... G06V 10/751

FOREIGN PATENT DOCUMENTS

CN 113628296 A 11/2021
CN 113850883 A 12/2021
(Continued)

OTHER PUBLICATIONS

Chen Xiaojun, et al., Research progress on reconstruction for magnetic particle imaging based on system matrix, Beijing Biomedical Engineering, 2020, pp. 196-202, vol. 39 No. 2.
(Continued)

*Primary Examiner* — Leon Viet Q Nguyen
(74) *Attorney, Agent, or Firm* — Bayramoglu Law Offices LLC

(57) ABSTRACT

A system for reconstructing a magnetic particle image based on a pre-trained model aims to address the influence by point spread function and reduce the computational and time costs, which results in low reconstruction accuracy, or high acquisition time and computational costs for high-precision images. The system is implemented by: generating a simulation system matrix; pre-training a pre-constructed neural network model, and fine-tuning a pre-trained neural network model by performing a downstream task; and inputting real data corresponding to the downstream task into the pre-trained neural network model after fine-tuning, thereby playing an auxiliary role to acquire a high-quality reconstructed MPI image. The system fits the relationship between different harmonics, which helps enhance frequency-domain information. The system has certain universality and can be generalized to a plurality of downstream tasks related to MPI image reconstruction, thereby acquiring high-quality reconstructed images through simple model fine-tuning.

8 Claims, 7 Drawing Sheets

(56) References Cited

FOREIGN PATENT DOCUMENTS

| CN | 113947642 A | 1/2022 |
| CN | 114723729 A | 7/2022 |
| CN | 114998471 A | 9/2022 |
| CN | 116030155 A | 4/2023 |
| CN | 116068468 A | 5/2023 |
| KR | 20220050758 A | 4/2022 |

OTHER PUBLICATIONS

Lin Yin, et al., Recent developments of the reconstruction in magnetic particle imaging, Visual Computing for Industry, Biomedicine, and Art, 2022, pp. 1-13, vol. 5 No. 24.

* cited by examiner

SYSTEM FOR RECONSTRUCTING MAGNETIC PARTICLE IMAGE BASED ON PRE-TRAINED MODEL

CROSS REFERENCE TO THE RELATED APPLICATIONS

This application is based upon and claims priority to Chinese Patent Application No. 202310753529.X, filed on Jun. 26, 2023, the entire contents of which are incorporated herein by reference.

TECHNICAL FIELD

The present disclosure belongs to the field of magnetic particle imaging (MPI), and specifically relates to a system for reconstructing a magnetic particle image based on a pre-trained model.

BACKGROUND

Accurately, and objectively, locating tumors and other lesions in clinical diagnosis and detection has always been a research hotspot and challenging issue internationally. Existing medical imaging technologies such as computed tomography (CT), magnetic resonance imaging (MRI), and single-photon emission computed tomography (SPECT) have problems such as radiation hazard, poor localization, and low precision. In recent years, a new tracer-based imaging method, namely magnetic particle imaging (MPI) has been proposed. MPI can accurately locate tumors or targets by detecting the spatial concentration distribution of super-paramagnetic iron oxide nanoparticles (SPIONs) harmless to human body through tomography technology. MPI features, high sensitivity, high temporal-spatial resolution, and high imaging depth three-dimensional (3D) imaging. It does not display anatomical structures and is not affected by background signals, so the intensity of the signal is directly proportional to the concentration of the tracer. Therefore, MPI is a new method with great potential for medical applications.

The current MPI technology is still in the development stage, and the hardware and algorithms are constantly improving, aiming to achieve high-quality image reconstruction through hardware improvements and algorithm optimization. Hardware improvements will often increase system complexity and reduce system stability, resulting in long implementation cycles and high complexity. For this reason, existing methods rely on algorithm optimization to improve image reconstruction quality. Existing reconstruction algorithms mainly include two categories: X-space reconstruction method and system matrix reconstruction method. The two methods reconstruct images by processing time-domain or frequency-domain signals of magnetic particle. The X-space reconstruction method has the advantage of fast reconstruction, but due to its principle, the method is often affected by the point spread function (PSF), resulting in low-resolution reconstructed images. The system matrix reconstruction method has the potential for obtaining high-quality reconstructed images, but the acquisition and calibration of the system matrix requires a lot of time and computational costs. Therefore, a universal algorithm enhancement framework is needed to effectively enhance time/frequency signals of magnetic particle, to improve the reconstruction quality and the time consumption of different reconstruction algorithms simultaneously.

In view of this, the present disclosure provides a system for reconstructing a magnetic particle image based on a pre-trained model.

SUMMARY

The present disclosure aims to solve the above problems in the prior art. The current magnetic particle imaging (MPI) technology is still in the development stage, and the hardware and algorithms are constantly improving, aiming to achieve high-quality image reconstruction through hardware improvements and algorithm optimization. Hardware improvements will often increase system complexity and reduce system stability, resulting in long implementation cycles and high complexity. In view of this, the present disclosure provides a system for reconstructing a magnetic particle image based on a pre-trained model. The system includes a MPI device, a signal processor, and a control processor, where a wired or wireless communication exists between the MPI device, the signal processor, and the control processor;

the control processor is configured to adjust a parameter of the MPI device and control the MPI device to scan a magnetic particle sample, through the wired or wireless communication;

the signal processor includes:

a simulation system generation module, configured to generate simulation system matrices of the magnetic particle imaging system with different parameters;

a first neural network model parameter acquisition module, configured to pre-train a pre-constructed neural network model according to the simulation system matrices, take a pre-trained neural network model as a first neural network model, and acquire a parameter of the first neural network model;

where, the first neural network model parameter acquisition module includes: a matrix conversion module, configured to convert the simulation system matrices obtained from the simulation system generation module into real-domain matrices as first matrices, initialize the all-1 matrices of a same size as the first matrices, set a value of a first preset percentage in the all-1 matrices to zero to acquire mask matrices, and multiply the mask matrices with the first matrices to acquire masked simulation system matrices as second matrices;

a recovered system matrix acquisition module, configured to take the first matrices as true value labels, divide the second matrices into a plurality of matrix blocks with an equal size, and take the plurality of matrix blocks as an input into the pre-constructed neural network model, where the pre-constructed neural network model includes a first encoder and a first decoder;

recovered system matrices are acquired as third matrices based on the plurality of matrix blocks through the pre-constructed neural network model;

a first loss function calculation module, configured to calculate a loss function between the recovered system matrices and the true value labels, and adjust a parameter of the pre-constructed neural network model according to the loss function;

a first loop module, configured to loop through the recovered system matrix acquisition module and the first loss function calculation module according to a set number of training epochs until training of the pre-constructed neural network is completed, take a trained pre-constructed neural network as the first neural network model, and acquire the parameter of the first neural network model;

the recovered system matrices are acquired as the third matrices based on the plurality of matrix blocks through the pre-constructed neural network model by:

converting the plurality of matrix blocks into one-dimensional vectors, encoding the one-dimensional vectors to acquire matrix block vectors, and adding learnable position embedding to the matrix block vectors to acquire encoded matrix block vectors with the position embedding, as first vectors;

inputting the first vectors into the first encoder to acquire first feature vectors; and mapping a channel number of the first feature vectors to a dimension of the first decoder, inputting the channel mapped first feature vectors into the first decoder to acquire second feature vectors, converting the second feature vectors into a plurality of two-dimensional matrix blocks, and splicing the plurality of two-dimensional matrix blocks into the third matrices;

where, the first encoder is configured to encode the plurality of matrix blocks to acquire the first feature vectors, and the first encoder includes a plurality of consecutive self-attention layers;

the self-attention layer includes a self-attention layer input terminal, a multi-head attention layer, a first addition unit, a first layer normalization layer, a feedforward network, a second addition unit, a second layer normalization layer, and a self-attention layer output terminal that are sequentially connected;

the self-attention layer input terminal is in a residual connection to the first addition unit, and an output terminal of the first layer normalization layer is in a residual connection to the second addition unit;

the multi-head attention layer includes a multi-head attention layer input terminal, Q parallel dot product attention blocks, a feature connection layer, a first fully connected layer, and a multi-head attention layer output terminal that are sequentially connected, where Q is an integer;

the dot product attention block includes a dot-product first fully connected layer, a dot-product second fully connected layer, and a dot-product third fully connected layer that are arranged in parallel; an output of the dot-product first fully connected layer and an output of the dot-product second fully connected layer are jointly connected to a matrix multiplication unit, and are sequentially connected to a normalization layer and a softmax layer; and an output of the softmax layer and the dot-product third fully connected layer are jointly connected to the matrix multiplication unit, and are connected to a dot product attention block output terminal;

the first decoder is configured to decode the first feature vectors to acquire the third matrices, and the first decoder includes a plurality of consecutive self-attention layers;

a third neural network model acquisition module, configured to generate a data set corresponding to a downstream task, pre-construct a neural network model corresponding to the downstream task as a second neural network model, input the parameter of the first neural network model into the second neural network model, and train the second neural network model loaded with the parameter of the first neural network model through the data set to acquire a third neural network model; and an image reconstruction module, configured to input acquired real input data collected by the MPI device into the third neural network model for enhancement, play an auxiliary role to acquire a reconstructed MPI image, and accurately locate a tumor or target based on the reconstructed MPI image, where if the downstream task is an X-space reconstruction related method, the input data is divided frames of one-dimensional frequency-domain signals acquired by performing Fourier transform on an acquired real noisy one-dimensional time-domain signal; and if the downstream task is a system matrix reconstruction related method, the input data is a collected low-quality system matrix.

In some preferred implementations, the simulation system matrix is generated by:

acquiring parameters, where the parameters include: gradient field G, excitation amplitude A, excitation frequency $f_D$, scanning frequency $f_F$, particle size D, and pixel size S;

calculating a size of an imaging field of view based on the gradient field G and the excitation amplitude A, acquiring the field of view, and dividing the field of view into N pixel blocks with an equal size based on the pixel size s according to a first preset threshold N;

placing the magnetic particle sample in the field of view, traversing the N pixel blocks, and acquiring an induced voltage signal each time when a magnetic particle moves to one of the pixel blocks, to acquire N induced voltage signals; and performing Fourier transform on the N induced voltage signals to acquire N spectrum sequences corresponding to the N induced voltage signals, extracting M frequency points of main frequency components and sideband components in each of the spectrum sequences, sequentially splicing the frequency points to acquire N one-dimensional spectrum vectors, and combining the N one-dimensional spectrum vectors into an M×N matrix as the simulation system matrix.

In some preferred implementations, when the scanning frequency $f_F$ is set based on a Lissajous trajectory, the scanning frequency $f_F$ is expressed as follows:

$$f_F = \frac{N_d}{N_d + 1} f_D;$$

where, $N_d$ denotes a trajectory density and is within a first threshold range; and when the scanning frequency $f_F$ is set based on a Cartesian trajectory, the scanning frequency $f_F$ is within a second threshold range, and the second threshold range is a set multiple of a third threshold range of the excitation frequency $f_D$.

In some preferred implementations, when the simulation system matrix is generated, a magnetic moment of the magnetic particle is set by a Langevin function $\mathcal{L}(X)$:

$$L(x) = \coth(x) - \frac{1}{x};$$

where, x denotes a dimensionless magnetic field.

In some preferred implementations, the image reconstruction module is further configured to acquire and train the second neural network model loaded with the parameter of the first neural network model based on an X-space reconstruction module; and the X-space reconstruction module includes:
- a one-dimensional time-domain signal acquisition module, configured to acquire phantom images and acquire one-dimensional time-domain signals corresponding to a particle in the phantom images, where the phantom images include images of handwritten numeral and letter, and images of dots;
- a signal conversion module, configured to perform Fourier transform on the one-dimensional time-domain signals to acquire the one-dimensional frequency-domain signals as model labels, superimpose noise on the one-dimensional time-domain signals to acquire the noisy one-dimensional time-domain signals, and perform Fourier transform on the noisy one-dimensional time-domain signals to acquire the noisy one-dimensional frequency-domain signals as the input into the second neural network model, where the second neural network model includes a second fully connected layer, a second encoder, and a second decoder;
- a first encoded data acquisition module, configured to divide the noisy one-dimensional frequency-domain signals into L equal-length segments, where the number L of the segments is consistent with a number of the matrix blocks, and input the noisy one-dimensional frequency-domain signals with the L segments through the second fully connected layer into the second encoder for encoding to acquire first encoded data;
- a denoising module, configured to input the first encoded data into the second decoder to acquire denoised data segments, and splice the plurality of denoised data segments into a denoised one-dimensional frequency-domain signals;
- a second loss function calculation module, configured to acquire a loss function between the denoised one-dimensional frequency-domain signals and the model labels, and adjust the second neural network model loaded with the parameter of the first neural network model according to the loss function; and
- a second loop module, configured to loop through the first encoded data acquisition module, the denoising module, and the second loss function calculation module according to a set number of loops to acquire the third neural network model.

In some preferred implementations, the noisy one-dimensional time-domain signal is calculated as follows:

$$u_n(t) = u(t) + u_G(t) + u_h(t);$$

where, $u(t)$ denotes a one-dimensional time-domain signal acquired by simulation, $u_G(t)$ denotes Gaussian noise, $u_h(t)$ denotes harmonic interference noise, and $u_n(t)$ denotes the noisy one-dimensional time-domain signal;

the harmonic interference noise $u_h(t)$ is calculated as follows:

$$u_h(t) = \sum_{n=1}^{N} A_n \sin(2\pi f_n t + \theta_n);$$

where, n denotes an n-th harmonic, $f_n$ denotes a harmonic frequency, $\theta_n$ denotes a random phase, where the random phase is uniformly distributed in $[0, 2\pi]$, and $A_n$ denotes amplitude of an additional harmonic;

$A_n$ is calculated according to a signal-to-interference ratio (SIR):

$$SIR = 20\log_{10}\left(\frac{\max_{f_n}|U_n(f_n)|}{A_n}\right);$$

where, SIR denotes a set noise level, and $U_n(*)$ denotes a bandwidth of the n-th harmonic of the one-dimensional frequency-domain signals;

the Gaussian noise $u_G(t)$ is calculated as follows:

$$SNR = 20\log_{10}\left(\frac{\max_{t}|u(t)|}{\sigma}\right);$$

where, SNR denotes signal-to-noise ratio, $\sigma$ denotes a standard deviation of the noise, and u(t) denotes the one-dimensional time-domain signal.

In some preferred implementations, the image reconstruction module is configured to acquire the second neural network model loaded with the parameter of the first neural network model based on a system matrix reconstruction module; and the system matrix reconstruction module includes:
- a matrix acquisition module, configured to generate high-quality system matrices and low-quality system matrices, and take the high-quality system matrices as the model labels and the low-quality system matrices as the input into the second neural network model, where the second neural network model includes a third fully connected layer, a third encoder, and a third decoder;
- a second encoded data acquisition module, configured to divide the low-quality system matrix into a plurality of matrix blocks, where a number of the matrix blocks corresponding to the low-quality system matrix is consistent with a number of corresponding matrix blocks in the simulation system matrix, and input the matrix blocks corresponding to the low-quality system matrix through the third fully connected layer into the third encoder for encoding to acquire second encoded data;
- a matrix splicing module, configured to input the second encoded data into the third decoder to acquire enhanced one-dimensional feature vectors, convert the enhanced one-dimensional feature vectors into a plurality of enhanced matrix blocks, and splice the plurality of decoded matrix blocks into enhanced system matrices;
- a third loss function calculation module, configured to calculate a loss function between the enhanced system matrix and the high-quality system matrix, and adjust the second neural network model loaded with the parameter of the first neural network model according to the loss function; and
- a third loop module, configured to loop through the second encoded data acquisition module, the matrix splicing module, and the third loss function calculation module according to a set number of loops to acquire the third neural network model.

In some preferred implementations, the high-quality system matrix and the low-quality system matrix are generated by:
placing the magnetic particle sample in the field of view, traversing the N pixel blocks, and acquiring the induced voltage signal each time when the magnetic particle moves to one of the pixel blocks, to acquire the N induced voltage signals;

performing Fourier transform on each of the induced voltage signals to acquire N spectrum sequences corresponding to each of the induced voltage signals, extracting M frequency points of main frequency components and sideband components in each of the spectrum sequences, sequentially splicing the frequency points to acquire the N one-dimensional spectrum vectors, and combining the N one-dimensional spectrum vectors into the M×N matrix as the high-quality system matrix; and downsampling the high-quality system matrix to acquire the low-quality system matrix.

The present disclosure has following beneficial effects:

The present disclosure establishes a general high-quality reconstruction framework for MPI through a pre-trained model. The present disclosure pre-trains a neural network model through system matrices and fits the relationship between different harmonics, which helps enhance frequency-domain information. Therefore, the present disclosure can assist the two reconstruction algorithms, namely X-space reconstruction method and system matrix reconstruction method to acquire high-quality reconstructed images quickly and efficiently. The present disclosure has certain universality and can be generalized to a plurality of downstream tasks related to MPI image reconstruction, so as to assist reconstruction algorithms to acquire high-quality reconstructed images through simple model fine-tuning.

BRIEF DESCRIPTION OF THE DRAWINGS

Other features, objectives and advantages of the present disclosure will become more apparent upon reading the detailed description of the non-restrictive embodiments with reference to the following drawings.

DETAILED DESCRIPTION OF THE EMBODIMENTS

Figure 1:
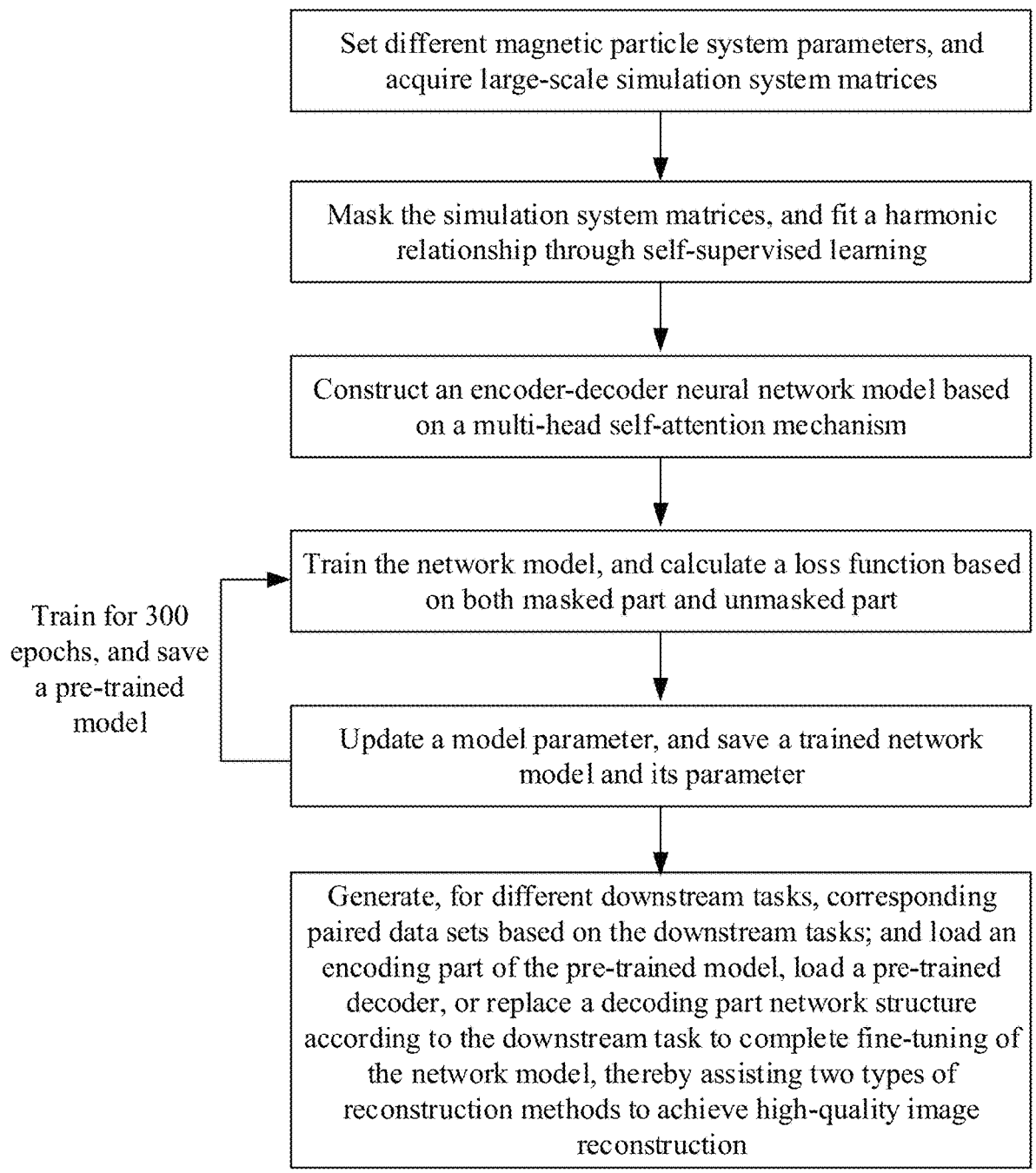
FIG. 1 is a schematic diagram showing a technical route of a system for reconstructing a magnetic particle image based on a pre-trained model according to the present disclosure.
Figure 2:
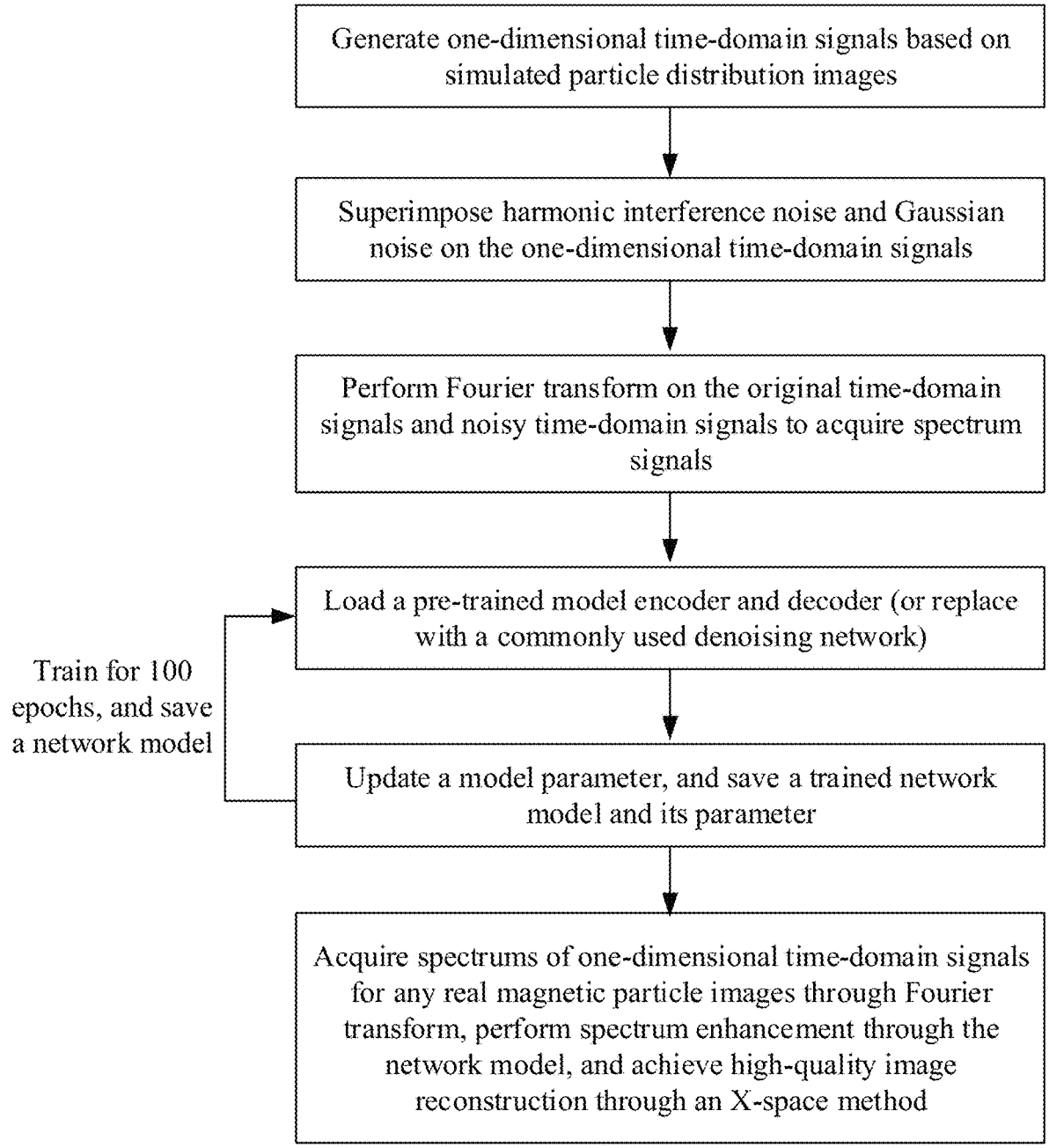
FIG. 2 is a schematic diagram showing a technical route of a downstream task for X-space spectrum enhancement by the system for reconstructing a magnetic particle image based on a pre-trained model according to the present disclosure.
Figure 3:
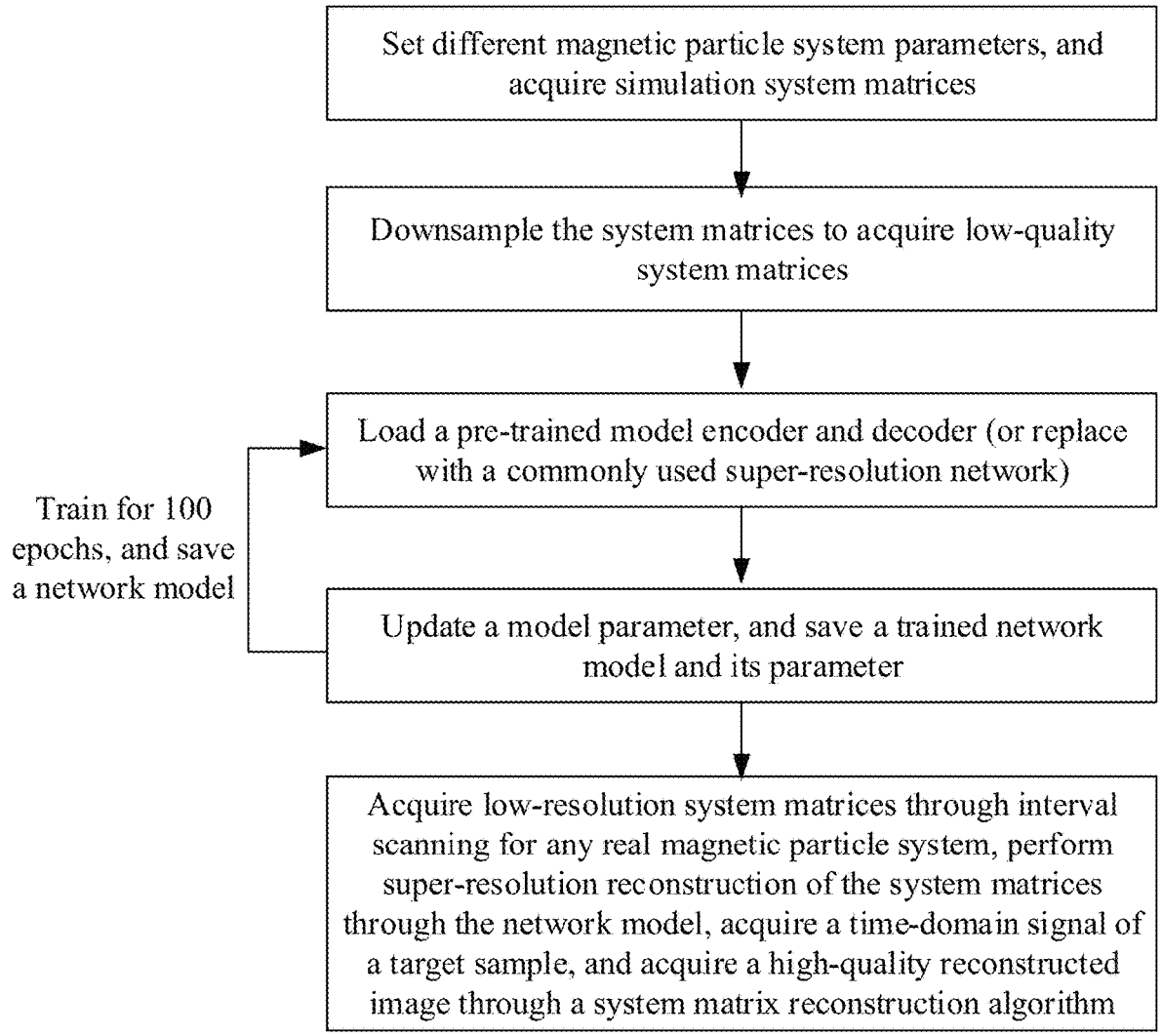
FIG. 3 is a schematic diagram showing a technical route of a downstream task for system matrix-based super-resolution reconstruction by the system for reconstructing a magnetic particle image based on a pre-trained model according to the present disclosure.

The present disclosure will be further described in detail below in conjunction with the drawings and embodiments. It should be understood that the specific embodiments described herein are merely intended to explain the present disclosure, rather than to limit the present disclosure. It should also be noted that, for convenience of description, only the parts related to the present disclosure are shown in the drawings.

It should be noted that the embodiments in the present disclosure and features in the embodiments may be combined with each other in a non-conflicting situation. The present disclosure will be described in detail below with reference to the drawings and embodiments.

An embodiment of the present disclosure provides a system for reconstructing a magnetic particle image based on a pre-trained model. As shown in FIGS. 1 to 7, the system includes a magnetic particle imaging (MPI) device, a signal processor, and a control processor.

A wired or wireless communication exists between the MPI device, the signal processor, and the control processor.

The control processor is configured to adjust a parameter of the MPI device and control the MPI device to scan a magnetic particle sample, through the wired or wireless communication.

Components of the signal processor are described as follows.

A simulation system generation module is configured to generate simulation system matrices of the magnetic particle imaging system with different parameters.

A first neural network model parameter acquisition module is configured to pre-train a pre-constructed neural network model according to the simulation system matrices, take a pre-trained neural network model as a first neural network model, and acquire a parameter of the first neural network model.

The first neural network model parameter acquisition module includes: a matrix conversion module, configured to convert the simulation system matrices obtained from the simulation system generation module into real-domain matrices as first matrices, initialize the all-1 matrices of a same size as the first matrices, set a value of a first preset percentage in the all-1 matrices to zero to acquire mask matrices, and multiply the mask matrices with the first matrices to acquire masked simulation system matrices as second matrices.

A recovered system matrix acquisition module is configured to take the first matrices as true value labels, divide the second matrices into a plurality of matrix blocks with an equal size, and take the plurality of matrix blocks as an input into the pre-constructed neural network model, where the pre-constructed neural network model includes a first encoder and a first decoder.

Recovered system matrices are acquired as third matrices based on the plurality of matrix blocks through the pre-constructed neural network model.

A first loss function calculation module is configured to calculate a loss function between the recovered system matrices and the true value labels, and adjust a parameter of the pre-constructed neural network model according to the loss function.

A first loop module is configured to loop through the recovered system matrix acquisition module and the first loss function calculation module according to a set number of training epochs until training of the pre-constructed neural network is completed, take a trained pre-constructed neural network as the first neural network model, and acquire the parameter of the first neural network model.

The recovered system matrices are acquired as the third matrices based on the plurality of matrix blocks through the pre-constructed neural network model. Specifically:

The plurality of matrix blocks are converted into one-dimensional vectors, the one-dimensional vectors are encoded to acquire matrix block vectors, and learnable position embedding is added to the matrix block vectors to acquire encoded matrix block vectors with the position embedding, as first vectors.

The first vectors are input into the first encoder to acquire first feature vectors.

A channel number of the first feature vectors is mapped to a dimension of the first decoder, the channel mapped first feature vectors are input into the first decoder to acquire second feature vectors, the second feature vectors are converted into a plurality of two-dimensional matrix blocks, and the plurality of two-dimensional matrix blocks are spliced into the third matrices.

The first encoder is configured to encode the plurality of matrix blocks to acquire the first feature vectors, and the first encoder includes a plurality of consecutive self-attention layers.

The self-attention layer includes a self-attention layer input terminal, a multi-head attention layer, a first addition unit, a first layer normalization layer, a feedforward network, a second addition unit, a second layer normalization layer, and a self-attention layer output terminal that are sequentially connected.

The self-attention layer input terminal is in a residual connection to the first addition unit, and an output terminal of the first layer normalization layer is in a residual connection to the second addition unit.

The multi-head attention layer includes a multi-head attention layer input terminal, Q parallel dot product attention blocks, a feature connection layer, a first fully connected layer, and a multi-head attention layer output terminal that are sequentially connected, where Q is an integer.

The dot product attention block includes a dot-product first fully connected layer, a dot-product second fully connected layer, and a dot-product third fully connected layer that are arranged in parallel. An output of the dot-product first fully connected layer and an output of the dot-product second fully connected layer are jointly connected to a matrix multiplication unit, and are sequentially connected to a normalization layer and a softmax layer. An output of the softmax layer and the dot-product third fully connected layer are jointly connected to the matrix multiplication unit, and are connected to a dot product attention block output terminal.

The first decoder is configured to decode the first feature vectors to acquire the third matrices, and the first decoder includes a plurality of consecutive self-attention layers.

A third neural network model acquisition module is configured to generate a data set corresponding to a downstream task, pre-construct a neural network model corresponding to the downstream task as a second neural network model, input the parameter of the first neural network model into the second neural network model, and train the second neural network model loaded with the parameter of the first neural network model through the data set to acquire a third neural network model.

An image reconstruction module is configured to input acquired real input data collected by the MPI device into the third neural network model for enhancement, play an auxiliary role to acquire a reconstructed MPI image, and accurately locate a tumor or target based on the reconstructed MPI image. If the downstream task is an X-space reconstruction related method, the input data is divided frames of one-dimensional frequency-domain signals acquired by performing Fourier transform on acquired real noisy one-dimensional time-domain signals. If the downstream task is a system matrix reconstruction related method, the input data is a collected low-quality system matrix.

If the downstream task is an X-space reconstruction related method, the input data is divided frames of one-dimensional frequency-domain signals acquired by performing Fourier transform on acquired real noisy one-dimensional time-domain signals. A real MPI one-dimensional time-domain signal is acquired and divided into a plurality of data based on a scanning period. The scanning period is a time taken for the field free line to scan the imaging field of view once. The acquired real MPI one-dimensional signal is subjected to a preprocessing operation based on a network input, including downsampling by truncation or upsampling by zero-padding. Divided frames of a plurality of data are acquired and input into the third neural network model to generate denoised results. The results are spliced into time-domain signals of a plurality of scanning periods. X-space reconstruction method is performed on the signals to acquire a reconstructed MPI image.

If the downstream task is a system matrix reconstruction related method, the input data is a low-quality system matrix acquired by performing Fourier transform on the one-dimensional time-domain signal. Specifically, sample points are placed at intervals and scanned to acquire the one-dimensional time-domain signal, and Fourier transform is performed to acquire the low-quality system matrix. The low-quality system matrix is input into the third neural network model to acquire a super-resolution high-quality system matrix. The time-domain signal of the target sample is acquired and subjected to the system matrix reconstruction algorithm to generate the reconstructed MPI image.

Figure 4:
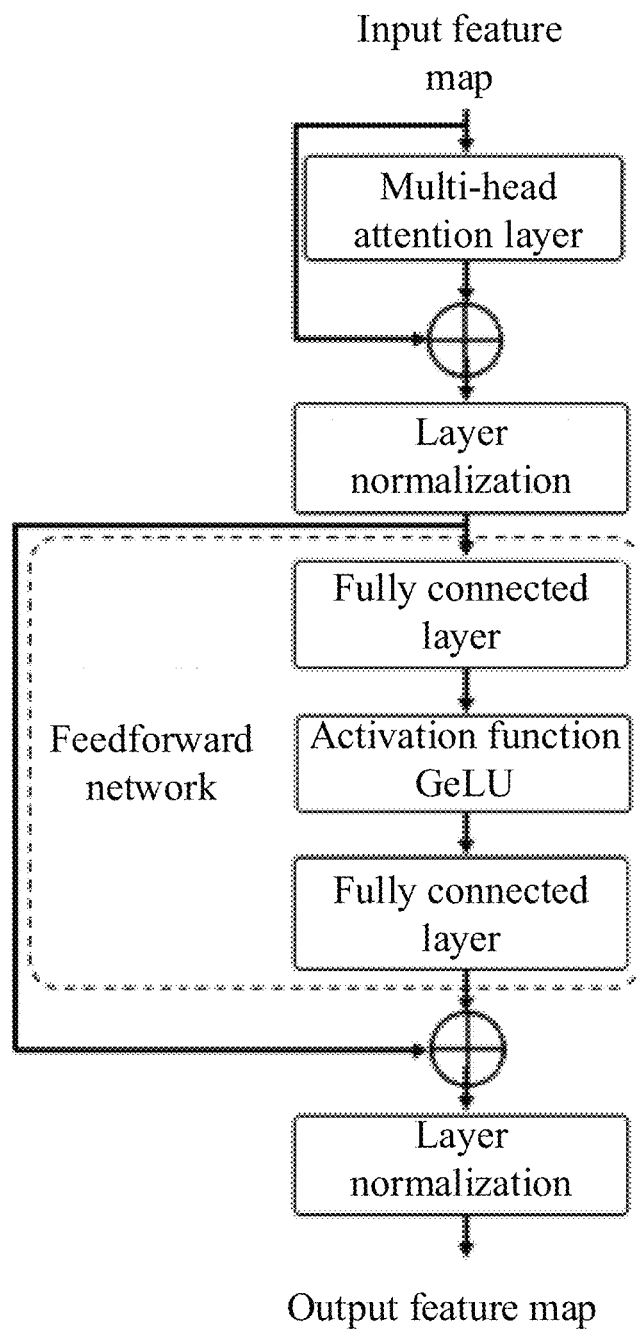
FIG. 4 is a structural diagram of a self-attention layer of the system for reconstructing a magnetic particle image based on a pre-trained model according to the present disclosure.
Figure 5:
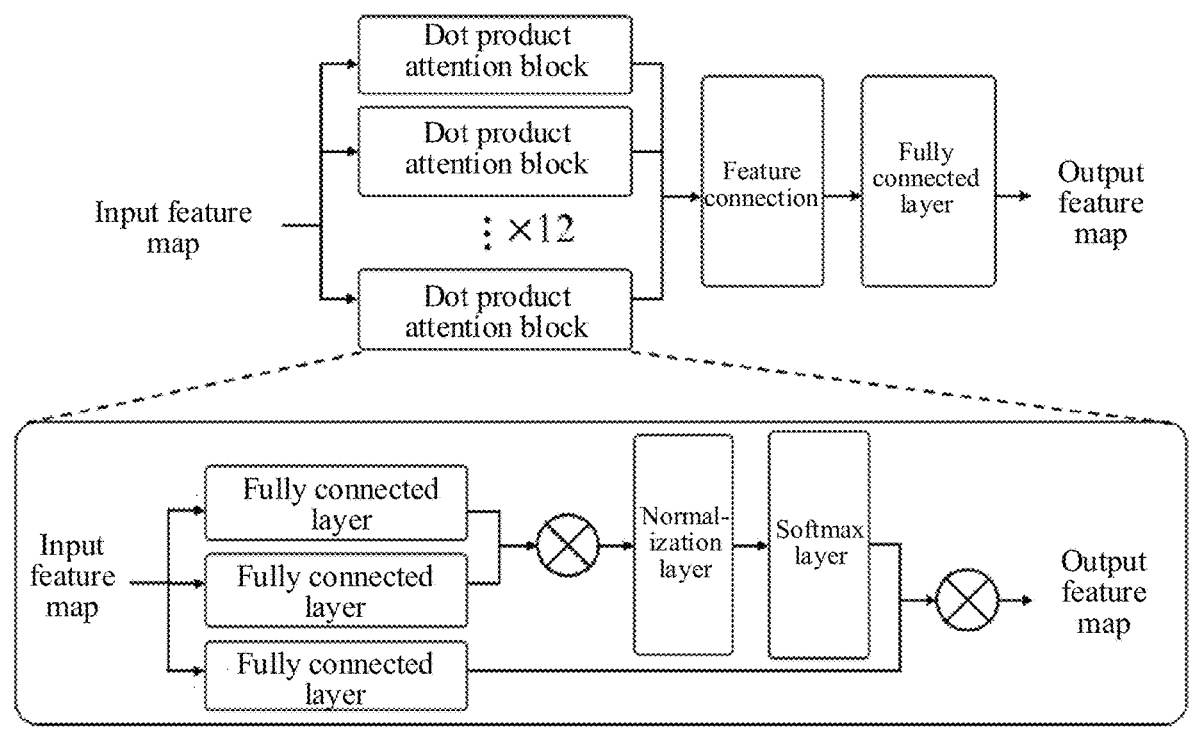
FIG. 5 is a structural diagram of a multi-head attention layer of the system for reconstructing a magnetic particle image based on a pre-trained model according to the present disclosure.
Figure 6:
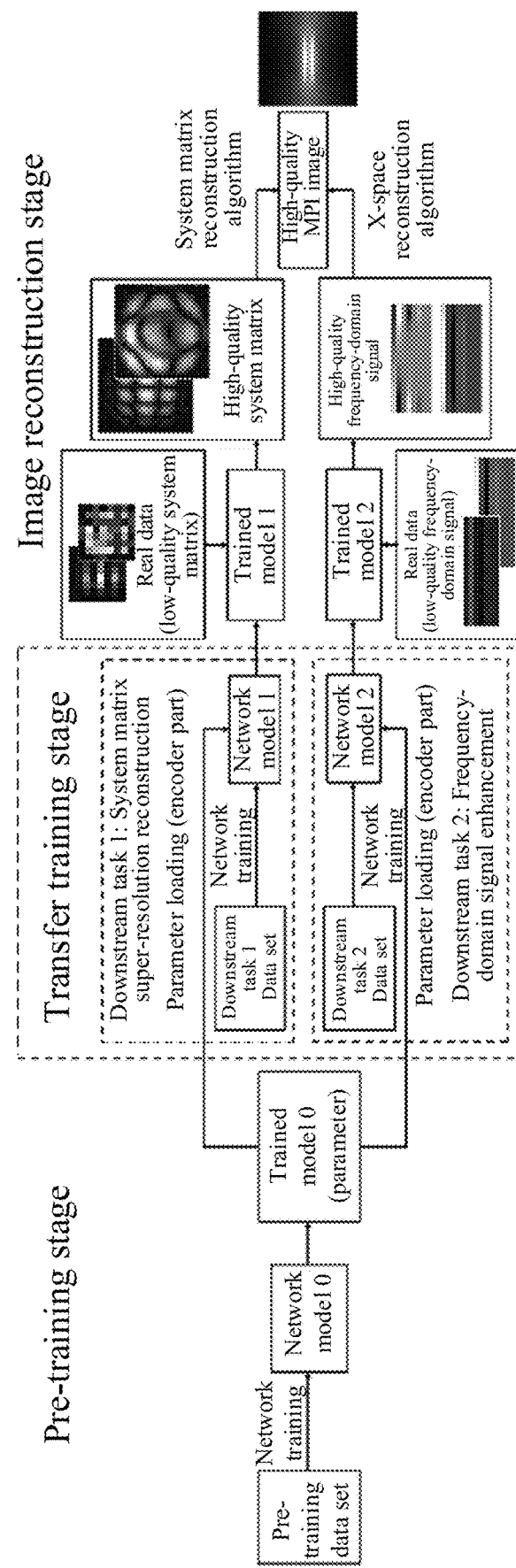
FIG. 6 is a flowchart of the system for reconstructing a magnetic particle image based on a pre-trained model according to the present disclosure.

As shown in FIGS. 4 and 5, the feature is input into the self-attention layer. First, the feature is processed through the multi-head attention layers. In each of the multi-head attention layers, the feature is first processed through 8 dot product attention blocks. In each of the dot product attention blocks, the feature is first processed through three dot-product fully connected layers. Output results of the first dot-product fully connected layer and the second dot-product fully connected layer are multiplied and then subjected to normalization and a softmax operation. After these operations, an output is multiplied by the output result of the third dot-product fully connected layer at the beginning of each block to acquire an output feature. The outputs of the 8 dot product attention blocks are subjected to a feature connection, and their channel dimension is changed through the first fully connected layer to acquire the output of the multi-head attention layer.

The output of the multi-head attention layer is directly added to the input of the self-attention layer, and then normalized by the layer normalization layer before entering the feedforward network. In the feedforward network, the input feature vector is first processed through a fully connected layer of the feedforward network to amplify the channel dimension. Then, the feature vector is processed by the activation function GELU and then by a fully connected layer of the feedforward network to reduce the channel dimension to be consistent with the input of the feedforward network. The obtained feature vector is directly added to the input feature vector of the feedforward network, and normalized by the layer normalization layer before it is output.

The operation of each self-attention layer is consistent, and the output of the first encoder is finally acquired after processing by the consecutive self-attention layers.

Figure 7:
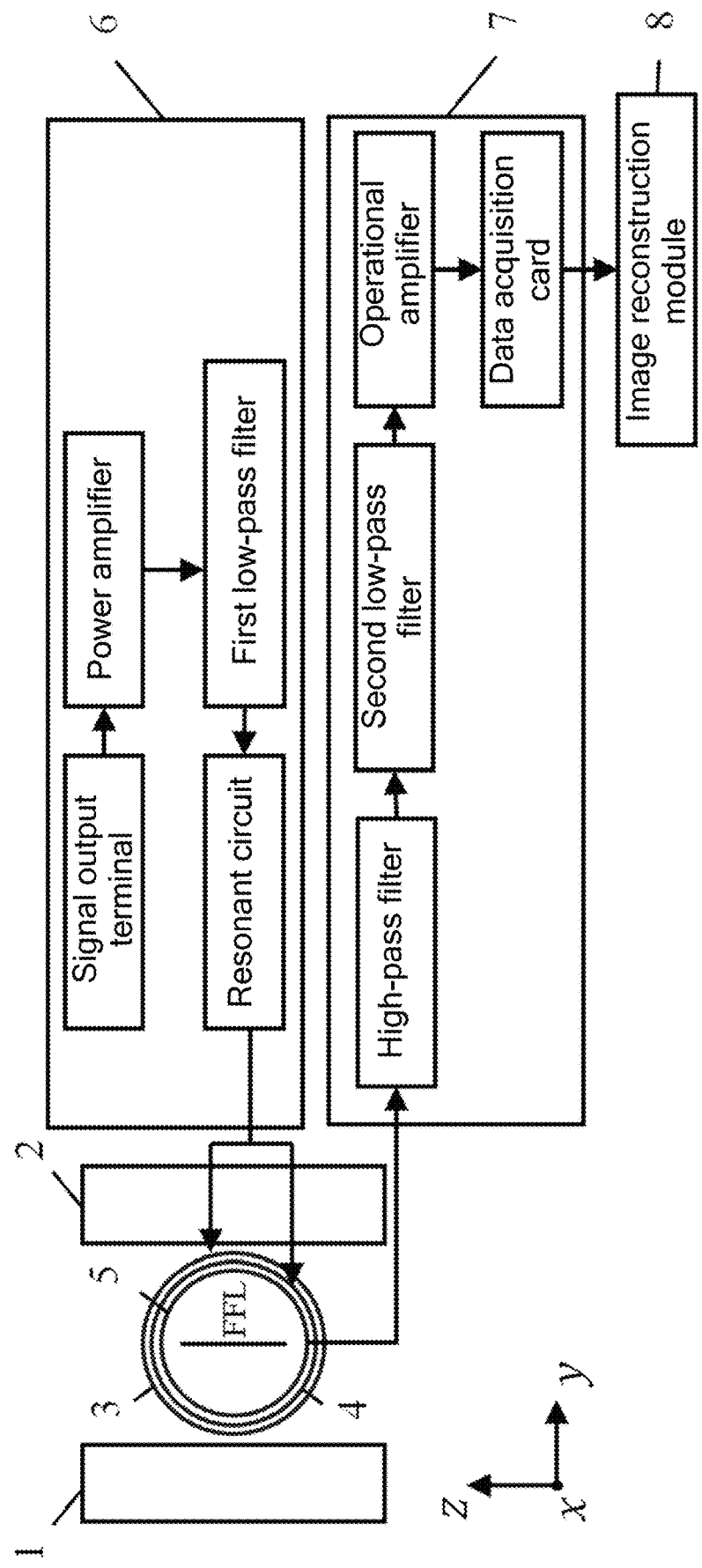
FIG. 7 is a structural diagram of a magnetic particle imaging (MPI) device in the system for reconstructing a magnetic particle image based on a pre-trained model according to the present disclosure.

As shown in FIG. 7, in the present disclosure, the MPI device is a magnetic particle image reconstruction device based on a pre-trained model, including a field free line (FFL) generation module, a dual-frequency drive module, current generation module 6, signal reception module 7, and image reconstruction module 8.

The field free line generation module is configured to generate a FFL. The field free line includes two pairs of permanent magnets with opposite polarities, namely first set of permanent magnets 1 and second set of permanent magnets 2. The two pairs of permanent magnets generate a FFL in a z-direction at a center.

The dual-frequency drive module includes first drive coil 4 and second drive coil 3 that are coaxially arranged and have an aperture direction in an x-axis direction. Copper shields are provided in the first drive coil 4 and the second drive coil 3 to isolate the mutual interference of the two electromagnetic coils. The dual-frequency drive module is configured to receive a current output by the current generation module 6 and drive the movement of the FFL to scan the imaging field of view. A high-frequency alternating current is applied to the first drive coil 4, and a low-frequency alternating current is applied to the second drive coil 3. The two currents simultaneously drive the movement of the FFL. The low-frequency current applied to the second drive coil 3 is conducive to generating sideband harmonics around main harmonics of the high-frequency in the frequency spectrum, which enhances spectrum resolution and expands the scanning field of view.

The dual-frequency drive module drives the FFL to move along a y-direction and scan the field of view.

The signal receiving module 7 includes receiving coil 5. The receiving coil 5 is configured to receive a signal generated by the FFL.

The signal receiving module 7 further includes a high-pass filter, a second low-pass filter, an operational amplifier, and a data acquisition card.

The high-pass filter is configured to receive an induced voltage signal acquired by the receiving coil 5 and suppress a direct feedthrough signal in the induced voltage signal.

The second low-pass filter is configured to receive a signal output by the high-pass filter, filter out high-frequency noise in the signal, and extract and output a signal within a set bandwidth.

The operational amplifier is configured to amplify a signal output by the second low-pass filter to generate an amplified signal as a first signal.

The data acquisition card is configured to receive the first signal, convert the first signal into a digital signal, and send the digital signal to the image reconstruction module 8.

The image reconstruction module 8 is configured to reconstruct an adjusted signal to acquire a magnetic particle distribution image.

The axis direction of the first drive coil 4 is the x-axis, the direction of the FFL is the z-axis direction, and the movement direction of the FFL is the y-direction. A midpoint of a perpendicular distance between the first set of permanent magnets 1 and the second set of permanent magnets 2 in the FFL generation module is taken as a symmetrical point.

The current generation module 6 includes a signal output terminal, a power amplifier, a first low-pass filter, and a resonant circuit.

The signal output terminal is configured to generate an excitation waveform required by the dual-frequency drive module.

The power amplifier is configured to convert the excitation waveform into an excitation current and output the excitation current to the first drive coil 4 and the second drive coil 3.

Due to the introduction of the two frequencies, i.e. low and high frequencies, the first low-pass filter is used for filtering. The first low-pass filter is configured to limit the current flowing into the first drive coil 4 and the second drive coil 3 to a set excitation frequency range, thereby reducing the generation of harmonic interference.

The excitation current is output to the resonant circuit through the first low-pass filter. The resonant circuit includes a plurality of inductors and capacitors. The resonant circuit is configured to change a resonant frequency by adjusting values of the inductors and capacitors, reducing impedance and power of a load through which the excitation current filtered by the first band-pass filter passes. An output terminal of the resonant circuit is connected to the first drive coil 4 and the second drive coil 3.

For downstream tasks of time-frequency spectrum enhancement, it is necessary to acquire time-domain signals. A moving sequence acquisition method is adopted. Specifically, the FFL is driven to move along the y-direction for one-dimensional scanning. The FFL is projected into points for one-dimensional imaging along the y-direction. Then, an imaging sample is moved along the x-direction. Each time, imaging is performed along the y-direction, and finally a two-dimensional imaging in an x-y plane is acquired. All the one-dimensional signals are spliced into a two-dimensional time-domain signal for enhancement, resulting in an enhanced two-dimensional image.

For a system matrix-based super-resolution reconstruction task, imaging is performed in a y-z plane. Specifically, first, a system matrix is acquired in the z-y plane. For each pixel block, signals are acquired at a plurality of angles. For example, when an n-th pixel block is acquired, first, the signal in the current state is acquired, then the FFL generation module is rotated around the symmetrical point by an angle, i.e., the FFL is rotated. Signals at a second angle are acquired. A golden angle sequence is used to rotate the FFL generation module within 360° to acquire signals at a plurality of angles at the pixel. These signals are subjected to Fourier transform and are spliced into a one-dimensional spectrum vector. After all the N pixels are acquired, N one-dimensional spectrum vectors are acquired and combined into an M×N matrix.

The method of acquiring the signal of the imaging sample is similar to the system matrix-based method. First, the imaging sample is moved to the center of the field of view. Signals under the same angle sequence are sequentially acquired as the system matrix and are spliced into a spectrum signal. Based on the acquired system matrix and signals of the imaging sample, the reconstructed image is acquired.

In order to acquire a higher-quality reconstructed image, more positions and angles are needed to acquire the system matrix. Therefore, the number of acquired pixel blocks and angles can be reduced, and super-resolution reconstruction is performed through a network model, such that the low-resolution system matrix is reconstructed into a high-resolution system matrix. The design can acquire a high-quality system matrix while greatly reducing acquisition time.

Preferably, the simulation system matrix is generated as follows.

Parameters are acquired, where the parameters include: gradient field G, excitation amplitude A, excitation frequency $f_D$, scanning frequency $f_F$, particle size D, and pixel size S.

A size of an imaging field of view is calculated based on the gradient field G and the excitation amplitude A, the field of view is acquired, and divided into N pixel blocks with an equal size based on the pixel size s according to a first preset threshold N.

The magnetic particle sample is placed in the field of view, the N pixel blocks are traversed, and an induced voltage signal is acquired each time when a magnetic particle moves to one of the pixel blocks, to acquire N induced voltage signals.

Fourier transform is performed on the N induced voltage signals to acquire N spectrum sequences corresponding to the N induced voltage signals, M frequency points of main frequency components and sideband components in each of the spectrum sequences are extracted and sequentially spliced to acquire N one-dimensional spectrum vectors, and the N one-dimensional spectrum vectors are combined into an M×N matrix as the simulation system matrix.

The particle size D is 5-70 nm, with an interval of 5 nm. The excitation frequency $f_D$ is 10-50 kHz, with an interval of 5 kHz. The gradient field G is 1-5 T, with an interval of 0.5 T. The excitation amplitude A is 1-10 mT, with an interval of 1 mT.

When changing the gradient field or excitation amplitude, the pixel size s is simultaneously changed to control the number of spatial points in the acquired system matrix, and 51×51 pixels in the field of view are maintained in the simulation, that is, N=2601.

In the M×N matrix, each row represents a same frequency point corresponding to different pixel block locations, and each column represents a spectrum vector corresponding to each pixel block. The matrix is a measurement matrix between the spatial distribution of magnetic particle concentration and the one-dimensional spectrum vector. For a Lissajous trajectory, the rule for selecting the frequency points is as follows:

$$f_k = \Delta f \cdot k;$$

$$\Delta f = \frac{f_F}{N_d};$$

$$N_d = \frac{f_F}{f_D - f_F};$$

$$k = N_d(m_x + m_y) + m_x;$$

$m_x$ and $m_y$ are positive integers between 1 and 18, so a total of 18×18=324 frequency points are selected. For a Cartesian trajectory, main harmonics of $1^{st}$-multiplication to $36^{th}$-multiplication frequency bands, and sideband harmonics each having a harmonic length of a frequency band being 4 both on the left and right of the main harmonics are selected. The excitation frequency $f_D$ is a fundamental frequency (the first main harmonic component), and a kth-multiplication main harmonic component is $kf_D$. The sideband harmonics are frequency points adjacent to the harmonics of the main frequency band, with 4 frequency points on each side, so a total of 36×(4+1+4)=324 frequency points are selected. Therefore, M=324.

A Debye relaxation model is added to the simulation process to simulate realistic particle signals.

Preferably, when the scanning frequency $f_F$ is set based on a Lissajous trajectory, the scanning frequency $f_F$ is expressed as follows:

$$f_F = \frac{N_d}{N_d + 1} f_D;$$

$N_d$ denotes a trajectory density and is within a first threshold range. The first threshold range is 19-99, with an interval of 10.

When the scanning frequency $f_F$ is set based on a Cartesian trajectory, the scanning frequency $f_F$ is within a second threshold range, and the second threshold range is a set multiple of a third threshold range of the excitation frequency $f_D$. The set multiple is 1/1,000-10/1,000, with an interval of 1/1,000. The third threshold range is 10-50 kHz, with an interval of 5 kHz.

Preferably, when the simulation system matrix is generated, a magnetic moment of the magnetic particle is set by Langevin function $\mathcal{L}(x)$:

$$\mathcal{L}(x) = \coth(x) - \frac{1}{x};$$

where, x denotes a dimensionless magnetic field.

Preferably, the image reconstruction module is further configured to acquire and train the second neural network model loaded with the parameter of the first neural network model based on an X-space reconstruction module. Components of the X-space reconstruction module are described as follows.

A one-dimensional time-domain signal acquisition module is configured to acquire phantom images and acquire one-dimensional time-domain signals corresponding to a particle in the phantom images, where the phantom images include images of handwritten numeral and letter, and images of dots.

A signal conversion module is configured to perform Fourier transform on the one-dimensional time-domain signals to acquire the one-dimensional frequency-domain signals as model labels, superimpose noise on the one-dimensional time-domain signals to acquire the noisy one-dimensional time-domain signals, and perform Fourier transform on the noisy one-dimensional time-domain signals to acquire the noisy one-dimensional frequency-domain signals as the input into the second neural network model, where the second neural network model includes a second fully connected layer, a second encoder, and a second decoder.

A first encoded data acquisition module is configured to divide the noisy one-dimensional frequency-domain signals into L equal-length segments, where the number L of the segments is consistent with a number of the matrix blocks, and input the noisy one-dimensional frequency-domain signals with the L segments through the second fully connected layer into the second encoder for encoding to acquire first encoded data.

A denoising module is configured to input the first encoded data into the second decoder to acquire denoised data segments, and splice the plurality of denoised data segments into denoised one-dimensional frequency-domain signals.

A second loss function calculation module is configured to acquire a loss function between the denoised one-dimensional frequency-domain signals and the model labels, and adjust the second neural network model loaded with the parameter of the first neural network model according to the loss function.

A second loop module is configured to loop through the first encoded data acquisition module, the denoising module, and the second loss function calculation module according to a set number of loops to acquire the third neural network model.

When the simulation system matrix is converted into a real-domain matrix, the simulation system matrix is a frequency-domain signal, which is a complex number. The real and imaginary parts are taken as two channels of input, which changes the original system matrix H×W (complex domain) to H×W×2 (real domain). The mask matrix is consistent for the real and imaginary parts of the simulation system matrix, so the size of mask matrix is H×W. The system matrix processed by the network uses the real and imaginary parts as two-channel real-domain data.

The mask matrix is retained as a basis for calculating the loss.

The first encoder adopts a Vision Transformer structure.

The matrix block is converted into a one-dimensional vector through a reshape function.

The loss function is calculated as follows. The mask matrices are multiplied with the third matrices to acquire the restored system matrices, corresponding to the unmasked part, as fourth matrices. The 0-1 conversion is performed on the mask matrices, that is, 0 becomes 1 and 1 becomes 0. The 0-1 conversion mask matrices are multiplied with the third matrices to acquire the restored system matrices corresponding to the masked part, as fifth matrices. Mean square error $l_1$ between the fifth matrices and the ground truth labels and mean absolute error $l_2$ between the fourth matrices and the ground truth labels are calculated. Final loss function is $l=l_1+l_2$, where A is a constant, which is 2.

The set number of training epochs is 300. In other words, the network training is performed for 300 epochs and a final model is retained as the pre-trained model, which is the first neural network model.

After the operation of the first encoded data acquisition module is completed, the parameter of the first neural network model is loaded into the second neural network, and the second neural network is fine-tuned.

The X-space reconstruction related method is limited by the spectrum resolution of the signal. When the signal-to-noise ratio of the acquired signal is low, the number of effective harmonic components is small, resulting in poor quality of the corresponding time-domain signal. As a result, the quality of the MPI image acquired by X-space reconstruction is limited. Spectrum enhancement can effectively improve spectrum resolution, increase the number of effective harmonic components, and thus improve the quality of the time-domain signal, resulting in a high-quality reconstructed MPI image.

Preferably, the noisy one-dimensional time-domain signal is calculated as follows:

$$u_n(t)=u(t)+u_G+u_h(t);$$

where, u(t) denotes a one-dimensional time-domain signal acquired by simulation, $u_G(t)$ denotes Gaussian noise, $u_h(t)$ denotes harmonic interference noise, and $u_n(t)$ denotes the noisy one-dimensional time-domain signal.

The harmonic interference noise $u_h(t)$ is calculated as follows:

$$u_h(t) = \sum_{n=1}^{N} A_n \sin(2\pi f_n t + \theta_n);$$

where, n denotes an n-th harmonic, a denotes a harmonic frequency, 0 denotes a random phase, where the random phase is uniformly distributed in [0,2π], and $A_n$ denotes amplitude of an additional harmonic.

$A_n$ is calculated according to a signal-to-interference ratio (SIR):

$$SIR = 20\log_{10}\left(\frac{\max_{f_n}|U_n(f_n)|}{A_n}\right);$$

where, SIR denotes a set noise level, and $U_n(*)$ denotes a bandwidth of the n-th harmonic of the one-dimensional frequency-domain signals.

The Gaussian noise $u_G(t)$ is calculated as follows:

$$SNR = 20\log_{10}\left(\frac{\max_t|u(t)|}{\sigma}\right);$$

where, SNR denotes signal-to-noise ratio, σ denotes a standard deviation of the noise, and u(t) denotes the one-dimensional time-domain signal.

Fourier transform is performed on the original one-dimensional time-domain signals u(t) and the noisy time-domain signals $u_n(t)$ to acquire one-dimensional frequency-domain signals as model labels and model input for the downstream task. Since the simulation is performed under ideal conditions, the original one-dimensional signals u(t) are not affected by any noise interference, and the frequency-domain signals have high quality, with a large number of available harmonics. The noisy signals are affected by noise, so the quality of the harmonics in the frequency-domain signals are reduced, for example, the signals are overwhelmed by noise or superimposed with noise interference. Supervised training is performed based on the pre-trained model to enhance the spectrum signals and achieve higher-quality reconstruction.

The second encoder part can use the structure of the first encoder. Since the downstream task is denoising, which is different from the model pre-training task, a commonly used denoising network structure can be used as the second decoder.

During the fine-tuning process, the set number of loops is 50-100 epochs, preferably 100 epochs, and then the final model is saved. The network training is supervised by calculating the loss function between the network output and the label.

Preferably, the image reconstruction module is configured to acquire the second neural network model loaded with the parameter of the first neural network model based on a system matrix reconstruction module. Components of the system matrix reconstruction module are described as follows.

A matrix acquisition module is configured to generate high-quality system matrices and low-quality system matrices, and take the high-quality system matrices as the model labels and the low-quality system matrices as the input into the second neural network model, where the second neural network model includes a third fully connected layer, a third encoder, and a third decoder.

A second encoded data acquisition module is configured to divide the low-quality system matrix into a plurality of matrix blocks, where a number of the matrix blocks corresponding to the low-quality system matrix is consistent with a number of corresponding matrix blocks in the simulation system matrix, and input the matrix blocks corresponding to the low-quality system matrix through the third fully connected layer into the third encoder for encoding to acquire second encoded data.

A matrix splicing module is configured to input the second encoded data into the third decoder to acquire enhanced one-dimensional feature vectors, convert the enhanced one-dimensional feature vectors into a plurality of enhanced matrix blocks, and splice the plurality of decoded matrix blocks into enhanced system matrices.

A third loss function calculation module is configured to calculate a loss function between the enhanced system matrices and the high-quality system matrices, and adjust the second neural network model loaded with the parameter of the first neural network model according to the loss function.

A third loop module is configured to loop through the second encoded data acquisition module, the matrix splicing module, and the third loss function calculation module according to a set number of loops to acquire the third neural network model.

After the operation of the matrix acquisition module is completed, the parameter of the first neural network model is loaded into the second neural network, and the second neural network is fine-tuned.

The set number of loops is 50-100 epochs, preferably 100 epochs, and then the final model is saved. The network training is supervised by calculating the loss function between the network output and the label.

The third decoder part can use the structure of the first decoder. Since the downstream task is super-resolution reconstruction, which is different from the model pre-training task, a commonly used super-resolution reconstruction network structure can be used as the third decoder.

Preferably, the high-quality system matrix and the low-quality system matrix are generated as follows.

The magnetic particle sample is placed in the field of view, the N pixel blocks are traversed, and an induced voltage signal is acquired each time when the magnetic particle moves to one of the pixel blocks, to acquire the N induced voltage signals.

Fourier transform is performed on each of the induced voltage signals to acquire the N spectrum sequences corresponding to each of the induced voltage signals, M frequency points of main frequency components and sideband components in each of the spectrum sequences are acquired and sequentially spliced to acquire the N one-dimensional spectrum vectors, and the N one-dimensional spectrum vectors are combined into the M×N matrix as the high-quality system matrix.

The high-quality system matrix is downsampled to acquire the low-quality system matrix.

The downsampling includes downsampling for the spectrum dimension M and the pixel block dimension N. The downsampling factor is set as 3×, 9×, etc. The downsampling is performed for the two dimensions with equal intervals, that is, different rows and columns are downsampled. The downsampled matrices are low-quality system matrices. The low-quality system matrices are taken as the model input, and the high-quality system matrices are taken as the model labels. The neural network completes the super-resolution reconstruction of the system matrices to accelerate the reconstruction process and acquire high-quality reconstructed images.

It should be noted that the system for reconstructing a magnetic particle image based on a pre-trained model in the above embodiments is only described by taking the division of the above functional modules as an example. In practical applications, the above functions can be completed by different functional modules as required, that is, the modules or steps in the embodiments of the present disclosure are further decomposed or combined. For example, the modules in the above embodiments may be combined into one module, or may be further divided into a plurality of sub-modules to complete all or part of the functions described above. The names of the modules and steps involved in the embodiments of the present disclosure are only for distinguishing each module or step, and should not be regarded as improper limitations on the present disclosure.

Terms "include" and any other similar terms are intended to cover non-exclusive inclusions, such that a process, a method, an article, or a device/apparatus including a series of elements not only includes those elements, but also includes other elements that are not explicitly listed, or also includes inherent elements of the process, the method, the article or the device/apparatus.

The technical solutions of the present disclosure are described in the preferred implementations with reference to the drawings. Those skilled in the art should easily understand that the protection scope of the present disclosure is apparently not limited to these specific implementations. Those skilled in the art can make equivalent changes or substitutions to the relevant technical features without departing from the principles of the present disclosure, and the technical solutions derived by making these changes or substitutions should fall within the protection scope of the present disclosure.

The invention claimed is:

1. A system for reconstructing a magnetic particle image based on a pre-trained model, comprising a magnetic particle imaging (MPI) device, a signal processor, and a control processor, wherein
 a wired or wireless communication exists between the MPI device, the signal processor, and the control processor;
 the control processor is configured to adjust a parameter of the MPI device and control the MPI device to scan a magnetic particle sample, through the wired or wireless communication; and
 the signal processor comprises:
 a simulation system generation module, configured to generate simulation system matrices of the magnetic particle imaging system with different parameters;
 a first neural network model parameter acquisition module, configured to pre-train a pre-constructed neural network model according to the simulation system matrices, take a pre-trained neural network model as a first neural network model, and acquire a parameter of the first neural network model;
 wherein the first neural network model parameter acquisition module comprises: a matrix conversion module, configured to convert the simulation system matrices obtained from the simulation system generation module into real-domain matrices as first matrices, initialize all-1 matrices of a same size as the first matrices, set a value of a first preset percentage in the all-1 matrices to zero to acquire mask matrices, and multiply the mask matrices with the first matrices to acquire masked simulation system matrices as second matrices;

a recovered system matrix acquisition module, configured to take the first matrices as true value labels, divide the second matrices into a plurality of matrix blocks with an equal size, and take the plurality of matrix blocks as an input into the pre-constructed neural network model, wherein the pre-constructed neural network model comprises a first encoder and a first decoder; and recovered system matrices are acquired as third matrices based on the plurality of matrix blocks through the pre-constructed neural network model;

a first loss function calculation module, configured to calculate a first loss function between the recovered system matrices and the true value labels, and adjust a parameter of the pre-constructed neural network model according to the first loss function;

a first loop module, configured to loop through the recovered system matrix acquisition module and the first loss function calculation module according to a set number of training epochs until training of the pre-constructed neural network is completed, take a trained pre-constructed neural network as the first neural network model, and acquire the parameter of the first neural network model;

wherein the recovered system matrices are acquired as the third matrices based on the plurality of matrix blocks through the pre-constructed neural network model by:

converting the plurality of matrix blocks into one-dimensional vectors, encoding the one-dimensional vectors to acquire matrix block vectors, and adding learnable position embedding to the matrix block vectors to acquire encoded matrix block vectors with the learnable position embedding, as first vectors;

inputting the first vectors into the first encoder to acquire first feature vectors; and mapping a channel number of the first feature vectors to a dimension of the first decoder, inputting the channel mapped first feature vectors into the first decoder to acquire second feature vectors, converting the second feature vectors into a plurality of two-dimensional matrix blocks, and splicing the plurality of two-dimensional matrix blocks into the third matrices;

wherein the first encoder is configured to encode the plurality of matrix blocks to acquire the first feature vectors, and the first encoder comprises a first plurality of consecutive self-attention layers;

each self-attention layer of the first plurality of consecutive self-attention layers comprises a self-attention layer input terminal, a multi-head attention layer, a first addition unit, a first layer normalization layer, a feedforward network, a second addition unit, a second layer normalization layer, and a self-attention layer output terminal that are sequentially connected;

the self-attention layer input terminal is in a residual connection to the first addition unit, and an output terminal of the first layer normalization layer is in a residual connection to the second addition unit;

the multi-head attention layer comprises a multi-head attention layer input terminal, Q parallel dot product attention blocks, a feature connection layer, a first fully connected layer, and a multi-head attention layer output terminal that are sequentially connected, wherein Q is an integer;

each of the Q parallel dot product attention blocks comprises a dot-product first fully connected layer, a dot-product second fully connected layer, and a dot-product third fully connected layer that are arranged in parallel; an output of the dot-product first fully connected layer and an output of the dot-product second fully connected layer are jointly connected to a matrix multiplication unit, and are sequentially connected to a normalization layer and a softmax layer; and an output of the softmax layer and the dot-product third fully connected layer are jointly connected to the matrix multiplication unit, and are connected to a dot product attention block output terminal; and the first decoder is configured to decode the first feature vectors to acquire the third matrices, and the first decoder comprises a second plurality of consecutive self-attention layers;

a third neural network model acquisition module, configured to generate a data set corresponding to a downstream task, pre-construct a neural network model corresponding to the downstream task as a second neural network model, input the parameter of the first neural network model into the second neural network model, and train the second neural network model loaded with the parameter of the first neural network model through the data set to acquire a third neural network model; and an image reconstruction module, configured to input acquired real input data collected by the MPI device into the third neural network model for enhancement, play an auxiliary role to acquire a reconstructed MPI image, and accurately locate a tumor or target based on the reconstructed MPI image, wherein when the downstream task is an X-space reconstruction related method, the input data is divided frames of one-dimensional frequency-domain signals acquired by performing Fourier transform on acquired real noisy one-dimensional time-domain signals; and when the downstream task is a system matrix reconstruction related method, the input data is a collected low-quality system matrix.

2. The system for reconstructing the magnetic particle image based on the pre-trained model according to claim 1, wherein the simulation system matrices are generated by:

acquiring parameters, wherein the parameters comprise: gradient field G, excitation amplitude A, excitation frequency $f_D$, scanning frequency $f_F$, particle size D, and pixel size s;

calculating the size of an imaging field of view based on the gradient field G and the excitation amplitude A, acquiring the imaging field of view, and dividing the imaging field of view into N pixel blocks with an equal size based on the pixel size S according to a first preset threshold N;

placing the magnetic particle sample in the imaging field of view, traversing the N pixel blocks, and acquiring an induced voltage signal each time when a magnetic particle moves to one of the N pixel blocks, to acquire N induced voltage signals; and performing Fourier transform on the N induced voltage signals to acquire N spectrum sequences corresponding to the N induced voltage signals, extracting M frequency points of main frequency components and sideband components in each of the N spectrum sequences, sequentially splicing the frequency points to acquire N one-dimensional spectrum vectors, and combining the N one-dimensional spectrum vectors into an M×N matrix as the simulation system matrices.

3. The system for reconstructing the magnetic particle image based on the pre-trained model according to claim 2, wherein when the scanning frequency $f_F$ is set based on a Lissajous trajectory, the scanning frequency $f_F$ is expressed as follows:

$$f_F = \frac{N_d}{N_d + 1} f_D;$$

wherein $N_d$ denotes a trajectory density and is within a first threshold range; and when the scanning frequency $f_F$ is set based on a Cartesian trajectory, the scanning frequency $f_F$ is within a second threshold range, and the second threshold range is a set multiple of a third threshold range of the excitation frequency $f_D$.

4. The system for reconstructing the magnetic particle image based on the pre-trained model according to claim 3, wherein when the simulation system matrix is generated, a magnetic moment of the magnetic particle is set by a Langevin function $\mathcal{L}(x)$:

$$\mathcal{L}(x) = \coth(x) - \frac{1}{x};$$

wherein x denotes a dimensionless magnetic field.

5. The system for reconstructing the magnetic particle image based on the pre-trained model according to claim 4, wherein the image reconstruction module is further configured to acquire and train the second neural network model loaded with the parameter of the first neural network model based on an X-space reconstruction module; and the X-space reconstruction module comprises:

a one-dimensional time-domain signal acquisition module, configured to acquire phantom images and acquire one-dimensional time-domain signals corresponding to a particle in the phantom images, wherein the phantom images comprises images of handwritten numeral and letter, and images of dots;

a signal conversion module, configured to perform Fourier transform on the one-dimensional time-domain signals to acquire the one-dimensional frequency-domain signals as model labels, superimpose noise on the one-dimensional time-domain signals to acquire the noisy one-dimensional time-domain signals, and perform Fourier transform on the noisy one-dimensional time-domain signals to acquire the noisy one-dimensional frequency-domain signals as the input into the second neural network model, wherein the second neural network model comprises a second fully connected layer, a second encoder, and a second decoder;

a first encoded data acquisition module, configured to divide the noisy one-dimensional frequency-domain signals into L equal-length segments, wherein the number of the L equal-length segments is consistent with a number of the matrix blocks, and input the noisy one-dimensional frequency-domain signals with the L equal-length segments through the second fully connected layer into the second encoder for encoding to acquire first encoded data;

a denoising module, configured to input the first encoded data into the second decoder to acquire a plurality of denoised data segments, and splice the plurality of denoised data segments into denoised one-dimensional frequency-domain signals;

a second loss function calculation module, configured to acquire a second loss function between the denoised one-dimensional frequency-domain signals and the model labels, and adjust the second neural network model loaded with the parameter of the first neural network model according to the second loss function; and a second loop module, configured to loop through the first encoded data acquisition module, the denoising module, and the second loss function calculation module according to a set number of loops to acquire the third neural network model.

6. The system for reconstructing the magnetic particle image based on the pre-trained model according to claim 5, wherein the noisy one-dimensional time-domain signal is calculated as follows:

$$u_n(t) = u(t) + u_G(t) + u_h(t);$$

wherein u(t) denotes a one-dimensional time-domain signal acquired by simulation, $u_G(t)$ denotes Gaussian noise, $u_h(t)$ denotes harmonic interference noise, and $u_n(t)$ denotes the noisy one-dimensional time-domain signal;

the harmonic interference noise $u_h(t)$ is calculated as follows:

$$u_h(t) = \sum_{n=1}^{N} A_n \sin(2\pi f_n t + \theta_n);$$

wherein n denotes an n-th harmonic, $f_n$ denotes a harmonic frequency, $\theta_n$ denotes a random phase, wherein the random phase is uniformly distributed in [0,2π], and $A_n$ denotes amplitude of an additional harmonic;

$A_n$ is calculated according to a signal-to-interference ratio (SIR):

$$SIR = 20\log_{10}\left(\frac{\max_{f_n}|U_n(f_n)|}{A_n}\right);$$

wherein SIR denotes a set noise level, and $U_n(*)$ denotes a bandwidth of the n-th harmonic of the one-dimensional frequency-domain signals; and the Gaussian noise $u_G(t)$ is calculated as follows:

$$SNR = 20\log_{10}\left(\frac{\max_{t}|u(t)|}{\sigma}\right);$$

wherein SNR denotes signal-to-noise ratio, σ denotes a standard deviation of the Gaussian noise, and u(t) denotes the one-dimensional time-domain signal.

7. The system for reconstructing the magnetic particle image based on the pre-trained model according to claim 4, wherein the image reconstruction module is configured to acquire the second neural network model loaded with the parameter of the first neural network model based on a system matrix reconstruction module; and the system matrix reconstruction module comprises:
- a matrix acquisition module, configured to generate high-quality system matrices and low-quality system matrices, and take the high-quality system matrices as the model labels and the low-quality system matrices as the input into the second neural network model, wherein the second neural network model comprises a third fully connected layer, a third encoder, and a third decoder;
- a second encoded data acquisition module, configured to divide the low-quality system matrices into a plurality of matrix blocks, wherein a number of the plurality of matrix blocks corresponding to the low-quality system matrix is consistent with a number of corresponding matrix blocks in the simulation system matrix, and input the matrix blocks corresponding to the low-quality system matrix through the third fully connected layer into the third encoder for encoding to acquire second encoded data;
- a matrix splicing module, configured to input the second encoded data into the third decoder to acquire enhanced one-dimensional feature vectors, convert the enhanced one-dimensional feature vectors into a plurality of enhanced matrix blocks, and splice the plurality of decoded matrix blocks into enhanced system matrices;
- a third loss function calculation module, configured to calculate a third loss function between the enhanced system matrices and the high-quality system matrices, and adjust the second neural network model loaded with the parameter of the first neural network model according to the third loss function; and
- a third loop module, configured to loop through the second encoded data acquisition module, the matrix splicing module, and the third loss function calculation module according to a set number of loops to acquire the third neural network model.

8. The system for reconstructing the magnetic particle image based on the pre-trained model according to claim 7, wherein the high-quality system matrices and the low-quality system matrices are generated by:
- placing the magnetic particle sample in the imaging field of view, traversing the N pixel blocks, and acquiring the induced voltage signal each time when the magnetic particle moves to one of the N pixel blocks, to acquire the N induced voltage signals;
- performing Fourier transform on each of the N induced voltage signals to acquire the N spectrum sequences corresponding to each of the N induced voltage signals, extracting M frequency points of main frequency components and sideband components in each of the N spectrum sequences, sequentially splicing the frequency points to acquire the N one-dimensional spectrum vectors, and combining the N one-dimensional spectrum vectors into the M×N matrix as the high-quality system matrix; and
- downsampling the high-quality system matrices to acquire the low-quality system matrices.

\* \* \* \* \*